United States Patent [19]

Weissman et al.

[11] Patent Number: 5,118,604
[45] Date of Patent: * Jun. 2, 1992

[54] RESTRICTION-FRAGMENT DNA PROBES AND PROBE CLUSTERS

[75] Inventors: Sherman M. Weissman, New Haven; Francis Collins, Cheshire, both of Conn.

[73] Assignee: Yale University, New Haven, Conn.

[*] Notice: The portion of the term of this patent subsequent to Dec. 1, 2004 has been disclaimed.

[21] Appl. No.: 539,028

[22] Filed: Jun. 15, 1990

[51] Int. Cl.$^5$ .................. C12Q 1/68; C12P 19/34; C07H 15/12

[52] U.S. Cl. .................. 435/6; 435/91; 536/27

[58] Field of Search .................. 435/6, 91; 536/27

[56] References Cited

U.S. PATENT DOCUMENTS 4,710,465 12/1987 Weissmann et al.

OTHER PUBLICATIONS

Little, P. F. R. et al., Proc. Natl. Acad. Sci. USA 82:3159 (1985).
Steinmetz, M. et al., Nature 300:35 (1982).
Rackwitz, H-R. et al. Gene 30:195 (1984).
Seed, B., Nucl. Acids Res. 11 (8):2427 (1983).
Serwer, P., Biochem. 19:3001 (1980).
Gusella, J. F. et al., Naute 306:234 (1983).
Dunn, R. J. et al., J. Biol. Chem. 256(12):6109 (1981).
Potter, H. et al., Proc. Natl. Acad. Sci. USA 76(3):1084 (1979).
Lau, Y-F. et al., Proc. Natl. Acad. Sci. USA 80:5225 (1983).

*Primary Examiner*—Robert A. Wax
*Assistant Examiner*—Scott A. Chambers
*Attorney, Agent, or Firm*—Peter J. Dehlinger; Gary R. Fabian

[57] ABSTRACT

A probe capable of binding by homologous base pairing independently to a pair of gene regions bordering the upstream and downstream sides of a pair of infrequent restriction endonuclease sites separated by between about 20-2,000 kilobases on a section of linear DNA. The probe is produced, according to the method of the invention by digesting the DNA section to completion with the selected endonuclease, and ligating the resulting fragments under conditions which favor end-to-end circularization, and selecting digest fragments of the large circular molecules which have end to end junctions. Also disclosed are method for mapping and ordering the positions of such probes, using another set of linking probes which span such rate cutting sites.

20 Claims, 4 Drawing Sheets

RESTRICTION-FRAGMENT DNA PROBES AND PROBE CLUSTERS

This application is a continuation of U.S. patent application for "Restriction-Fragment DNA Probes and Probe Clusters," Ser. No. 858,961, filed May 2, 1986, which was a continuation-in-part of U.S. Pat. No. 4,710,465, issued Dec. 1, 1987.

FIELD OF THE INVENTION

The present invention relates to gene probes suitable for use in gene mapping, and to methods of making and using the probes.

REFERENCES

1. Robertson, M., *Nature* (1983), 306:733.
2. Rabbitts, T. H., et al, *Nature* (1983), 306:760.
3. Heisterband, N., et al, *Nature* (1983), 306:239.
4. Bartram, C. R., et al, *Nature* (1983), 306:277.
5. Kan, Y. W., et al, *Proc Natl Acad Sci* (USA) (1983), 75:5631.
6. Humphries, S. E., et al, *Med Bull* (1983), 39:343.
7. Orkin, S. H., et al, *Nature* (1982), 296:627.
8. Orkin, S. H., et al, *Prog Hematol* (1983), 13:49.
9. Davies, K. E., et al, *Nucleic Acids Res* (1983), 11:2303.
10. Murray, J. M., et al, *Nature* (1982), 300:69.
11. Gusella, J. F., et al, *Nature* (1983), 306:234.
12. Steinmetz, M., et al, *Nature* (1982), 300:35.
13. Hayes, C. E., et al, *Science* (1984), 223:559.
14. Zabel, B. H., et al, *Proc Natl Acad Sci* (USA) (1983), 80:6932.
15. Botstein, D., et al, *Am J Human Genetics* (1980), 32:314.
16. Moller, G. (ed), *Immuno Rev* (1983), 70.
17. Erlich, H. A., et al, *Am J Human Genetics* (1980), 80:2300.
18. Maniatis, T., et al, *Molecular Cloning: A Laboratory Manual*, Cold Spring Harbor Laboratory (1982), 280.
19. Blin, N., et al, *Nucleic Acids Research* (1976), 3:2302.
20. Maniatis, op cit, 282.
21. Fangman, W. L., *Nucl Acids Res* (1978), 5:653.
22. Schwartz, D. C., et al, *Cold Sp HSQB* (1983), 7:189; Schwartz, D. C., and Cantor, C. R., *Cell* (May 1984), 37:67-75.
23. Dugaiczyk, A., et al, *J Mol Biol* (1975), 96:171.
24. Ryan, M. J. et al, *J. Biol Chem* (1979), 254:5817.
25. Maniatis, op cit, p. 300.
26. Langer, P. R., et al, *Proc Natl Acad Sci* (USA) (1981), 78:6633.
27. Hood, L., et al, *Cell* (1982), 28:685.
28. Maniatis, op cit pp. 187, 211.
29. Kraus, J., and Rosenberg, L. E., *Proc Natl Acad Sci* (USA) (1982), 79:4015.
30. Sood, A. K., et al, *Proc Natl Acad Sci* (USA) (1981), 78:616.
31. Das, H. K., et al, *Proc Natl Acad Sci* (USA) (1983), 80:1531.
32. Seed, B., *Nucleic Acids Res* (1983), 11:2427.
33. Barker, D., et al, *Cell* (1984) 36:1.
34. Steinmetz, M., et al, *Science* (1984), 222:727.
35. Kaufman, J. F., et al, *Cell* (1984), 36:1.
35a. Gladstone, P., et al, *Proc Natl Acad Sci* (USA) (1982), 79:1235.
36. Maniatis, op cit, p. 284.
37. Ish-Horowicz, et al, *Nucleic Acids Res* (1981), 9:2989.
38. Grosveld, F. G., et al, *Nucleic Acids Res* (1982), 10:6715.
39. Maniatis, op cit, p. 115.
40. Maniatis, op cit, p. 382.
41. Maniatis, op cit, p. 109.
42. Maniatis, op cit, p. 304.
43. Maniatis, op cit, p. 392.
44. Godson, G. N., in *Methods of DNA and RNA Sequencing*, ed. S. M. Weissman (New York: Praeger, 1983), pp. 69-111.
45. Bayer, E. A., and Wilchek, M., *Methods Biochem Analysis* (1980), 26:1.
46. Harper, M. E., and Saunders, G. F., *Chromosoma* (Berlin) (1980), 83:431.

BACKGROUND

Gene localization on chromosomes and an understanding of gene organization within large gene groups have become important areas of study in human genetics. A major application of gene localization is in understanding and predicting certain disease states. For example, translocation of marker genes from one chromosomal region to another may play a role in the development of cancer cells. One of the known oncogenes in man and rodents, termed myc, has been localized to a chromosome region which shows a consistent translocation from its normal chromosomal environment to one of three other chromosomes in certain forms of tumors such as Burkitt's lymphoma. Because of the location of the genes for immunoglobulins was previously known, it could be determined that the myc chromosome segment always became translocated to a second chromosome region containing immunoglobulin genes. Further studies have shown that the myc oncogene is, in fact, located close to the boundary of the translocation point, suggesting that a basic mechanism and causation of this lymphoma is the movement of the oncogene from its normal chromosome environment to an immunoglobulin gene environment in a cell where the immunoglobulin genes are being actively expressed (reviewed in references 1 and 2). Similarly, translocation of the Abl oncogene may be a major determinant of chronic myelocytic leukemia (references 3 and 4).

Another important application of gene localization is in identifying and furthering an understanding of inheritable disorders. Restriction endonuclease analysis of genomic RNA has made it possible to identify DNA polymorphisms which are linked closely to normal or mutated genes associated with available probes (reviewed in references 5, 6). The relationship between DNA polymorphisms and disease states was shown originally in studies on hemoglobinopathies, where certain polymorphisms are more frequent in patients with sickle cell disease, and where certain varieties of thalassemia are more commonly associated with specific combinations of restriction sites in intergenic DNA (references 7, 8). More recently, systematic studies have uncovered polymorphic DNA sites that are linked to and flank the locus of mutations which are responsible for Duchenne's muscular dystrophy (references 9, 10), and a fortuitously discovered probe associated with Huntington's disease has been used to identify polymorphic DNA which is closely linked to the gene responsible for Huntington's disease (reference 11). The probe makes it possible to diagnose people who carry the gene for Huntington's disease before the onset of the disease.

Heretofore, gene localization has been approached either by classical studies on gene linkage related to inheritance, or by microscopy and banding techniques for chromosomes. In the classical genetics approach, the frequency of co-inheritance of one phenotype trait, whose gene location is unknown, with a phenotypic trait whose gene location is known provides a measure of the linkage (distance) between the two genes, and this distance provides a rough measure of the relative chromosome positions of the two phenotypic genes. This classic genetic approach is severely limited in man, where controlled breeding is not possible, and where family studies on the inheritability of phenotypic disorders must therefore be relied on. Family studies in man and even genetic studies in inbred strains of mammals are generally unable to resolve gene linkages located closer than about 5 to 10 million base pairs apart, and can give aberrant results that cannot be readily understood until the actual physical structure of the gene is known. As an example of the latter problem, the I-J gene of suppressor lymphocyte surface antigen was initially considered to be one of the genes of the major histocompatibility complex (MHC), and this error was only corrected when portions of the MHC were actually cloned and partially sequenced (references 12, 13).

Genomic DNA regions of unique sequence can, in principle, be localized on a chromosome by in situ hybridization using single-copy DNA probes. In situ hybridization of nucleic acid probes to spreads of polytene chromosomes in Drosophila have been remarkably successful. The polytene chromosomes, which may be amplified over a thousand fold, allow site-specific binding of up to a thousand or more probes at the same location, making probe detection by autoradiography or by fluorescence or enzyme-reporter microscopy quite straightforward. Unfortunately, in situ hybridization to single-copy genes in human DNA is much more difficult to detect, since only a single site is available for probe binding, and can only be identified autoradiographically with relatively long periods of exposure and by counting grains over many chromosome samples to obtain a sufficient distribution of grains to verify probe localization. With rare exceptions, and particularly where only non-polytene chromosomes are available, the in situ hybridization technique cannot distinguish between sequences located closer than about 5 to 10 million base pairs apart (reference 14), comparable to the resolution achievable with phenotypic markers in classical genetic studies. The in situ hybridization technique for locating genes on a chromosome are also subject to artifactual errors such as a tendency for grains to accumulate at the tip or at the center of a chromosome. Such an artifact may account for the still conflicting data from in situ hybridization studies as to whether the beta globin system is located near the tip of chromosomal 11, or closer to the centromere.

In studies on polymorphic DNA regions, discussed above, it has been possible heretofore to localize identified polymorphisms only in the relatively few chromosome regions for which marker probes have been available, such as in the MHC region. In principle, if a complete family of probes spaced evenly along the genome were available, it would be possible to screen individuals for inherited dominant or even recessive disorders, and by comparing many DNA polymorphic sites in the affected individuals and unaffected family members, to localize and derive markers (probes) closely linked with every disorder. This theory has been discussed previously (reference 15). Since there are approximately 3,000 centimorgans of recombination distance distributed along the human genome, 300 evenly spaced markers would provide a marker for every 10 centimorgans, and 600 markers, for every 5 centimorgans. The probability of recombination between such a polymorphic marker and the given disease marker would be less than 1 in 20 in each generation. This set of 300 or 600 markers would greatly facilitate localization and identification of the precise genetic effects in gene regions responsible for these inheritable effects.

In order to generate such DNA probes for identifying polymorphic fragments by prior art techniques, many random DNA segments must be analyzed to see which ones provide polymorphic markers. Each one of these markers must be localized by the in situ hybridization technique described above, or by techniques involving hybridization and detection in a variety of somatic hybrid cell lines containing various human chromosomes or segments of chromosomes, or by hybridization to probes made from assorted chromosome libraries. The latter method is relatively inefficient due to the small amount of DNA that can be obtained in chromosomal sorting procedures. Statistical studies indicate that 900 or more probes would have to be examined in this way in order to obtain a 98% to 99% coverage of the human genome at the desired space intervals, a task that would be exceedingly difficult at best.

Considering now investigations of gene organization in multi-gene arrangements on chromosomes, the best-studied example is the human MHC, which appears to contain at least 40 to 50 class I-like genes, and at least 12 to 20 class II-like genes or pseudo-genes. It is known that the MHC system is highly polymorphic from individual to individual, and that particular alleles of class I or class II genes are associated with a predisposition towards a wide variety of diseases (references 16, 17). The association of polymorphisms with particular disease states may be due to polymorphisms within the known genes of the MHC, or, alternatively, to polymorphisms in presently unidentified class I or class II-type genes, or possibly unrelated genes interspersed within the class I or class II system. Therefore, a complete characterization of all the genes contained within this cluster, and their linear relationship with one another, would make it possible to predict which genes are most likely to be closely associated with particular diseases.

A study of the relationship among genes in a gene cluster or family can lead to greater understanding of gene diversity, gene interaction, and even the identification of previously unrecognized gene products. It is known, for example, that at least two pituitary hormones are encoded by genes contained in a gene cluster. Mapping the genes in this cluster has the potential to uncover DNA sequences that are potential genes of other known pituitary hormones and also genes for hormone-like substances that have not been previously recognized, but which arose during evolution by tandem duplication of preexisting genes for hormones.

As another example, it is known that there are many interferon-like genes in a cluster for one of the interferon types; similar clusters for interleukin-2 and other lymphokine genes, as well as for colony stimulating factor and nerve growth factors may be identified. Growth factors specific for several different cell types have been reported and it is possible that by mapping genes clustered about the growth factor genes, genes encoding other colony-stimulating factors or the like can be identified.

Similarly genes for additional coagulation factors, serum proteins, protease inhibitors, transcription or replication factors, cell membrane receptors, immunoglobulin variable or constant regions, and other cell type-specific surface antigens could well be identified by a practical method for surveying gene clusters.

The organization of genes within a gene family has been approachable, heretofore, generally at two levels of resolution. One is the resolution which can be obtained by classical studies of gene linkage during inheritance. As noted above, classical genetic techniques are unable to distinguish phenotypic markers located closer than about 5 to 10 million base pairs apart. The second level of resolution is that accessible by more recently developed recombinant DNA techniques. In a typical procedure, a genomic DNA insert which has been identified, for example, by hybridization with a selected gene probe, is characterized as to restriction sites and/or base sequence. Currently, the largest block of DNA that can be cloned intact is about 40 kilobases. The only method available in the prior art of extending the cloned sequence (beyond this 40 kilobase limit) is a technique known as chromosomal walking, in which the ends of the cloned insert are identified, radiolabeled, and used as probes to isolate, from a library of cloned DNA inserts, one or more inserts having a region of overlap with the end region(s) of the original insert. On the average, the radiolabeled end probes will identify inserts whose regions of overlap lie near the midpoint of the overlapping inserts. This means, for inserts of 40 kilobases, each additional insert isolated will extend the map region only about 20 kilobases.

The chromosomal walking technique is obviously quite tedious, in that each extension of the map requires screening a genomic DNA library, characterizing the restriction endonuclease sites and/or sequence of the probe-identified insert to locate the new insert in the map, and may require producing new end probes. Further, if one or more of the probes which are used in the procedure are non-unique sequences, these in turn will select for more than one site and cause apparent branching in the map. The maximum map distance that has been achieved to date by this method is about 200 kilobases, in a molecular map of an immune response region of MHC, in which 18 overlapping inserts were identified (reference 12). This was a particularly favorable system, since several probes scattered through the cluster were available.

It is thus apparent that examining gene relationships in a gene region of up to 200 kilobases is generally difficult and uncertain by prior art methods; and neither classical-genetic nor prior art cloning techniques are suited to resolving gene relationships in the range between about 200 kilobases and up to several thousand kilobases.

SUMMARY OF THE INVENTION

The present invention provides novel gene probes and gene probe clusters which can be readily designed and used for studying questions of gene localization and organization which have been largely inaccessible by prior art genetic analysis methods. In particular, the probe and methods are useful for studying gene mapping and relationships in a size range between about 100 and 2,000–5,000 kilobases.

A specific object of the invention is to provide a probe, also referred to herein as a hopping probe, which is capable of binding by base pair homology to the opposite end regions of a long DNA restriction fragment which may be up to a 1,000 or more kilobases in length.

A related object of the invention is to provide a method of using such hopping probes for constructing a restriction map of the corresponding long restriction fragment.

Another specific object of the invention is to provide a cluster of such hopping probes, each constructed for binding by base-pair homology to the end regions in each of a series of such long restriction fragments produced by cutting a genomic DNA section at an infrequent restriction site.

Still another object of the invention is to provide improved methods for generating a second cluster of probes, referred to herein as linking probes, each of which is capable of binding by homologous recombination to a region of such linear DNA section which spans one of such infrequent restriction sites.

A related object of the invention is to provide a method which uses the cluster of hopping and linking probes for constructing a map of the infrequent cutting sites along the linear DNA section.

The co-owned parent U.S. Pat. No. 4,710,465 discloses a novel gene probe constructed for binding by homologous base pairing independently to first and second gene regions which are spaced from one another on a linear strand or section of DNA by between about 20–2,000 kilobases, and which each have a defined upstream-to-downstream orientation in the DNA section. The probe is composed of a first segment derived from one end portion of a linear fragment of the DNA section which has the first and second gene regions at its opposite ends, and a second segment derived from the opposite end portion of the DNA fragment. The second segment is connected at its downstream end, as defined by the upstream-to-downstream orientation in the DNA section, to the upstream end of the first segment. The length of the probe is substantially less than that of the linear segment from which the probe is derived, and of a size that can be cloned in a suitable cloning vector.

The two segments in the probe may be connected by direct ligation, or through a marker segment which allows selection and/or isolation of the probe. In one embodiment of the probe invention, the marker segment includes a suppressor tRNA which allows for selection of a phage vector containing the probe in a suppressor (−) host. In another embodiment, the marker segment includes a cos site which allows for selection of a cosmid vector containing the probe as an insert. In still another embodiment, the marker segment includes a ligand by which the probe can be isolated by specific binding to an anti-ligand.

The probe described in the parent application is constructed, according to the method therein, by first treating a section of genomic DNA with an endonuclease, under conditions which yield random-size fragments whose sizes are predominantly between about 20–2,000 kilobases. The preferred procedure for fragmenting the DNA section described in the earlier application is by partial endonuclease digestion. Once formed, the DNA fragments are ligated under low-concentration conditions which produce predominantly circularized single-fragment species joined end-to-end. These circularized genomic fragments are then are digested with one or more selected restriction endonucleases to release relatively small digest fragments, some of which will contain such end-to-end connections. The digest fragments are cloned and then selected for those containing the end-to-end connections, yielding the probes which can bind by homologous base pairing to opposite end regions of the genomic fragments from which the probes were derived. The circularization may be carried out in the presence of a selectable marker, to allow for selection of digest fragments containing the desired end-to-end junction.

The probe method is valuable, for example, when a probe for a localized gene region is known, and it is desired to generate one or more probes which can bind to regions located between 20–2,000 kilobases from the known gene region. Here the partial digest fragments can be sized, prior to fragment circularization, to yield junction probes which bind (a) to the known gene region and (b) to a gene region a selected 20–2,000 kilobases distance from the known gene region. The advantage of the method is seen by comparison with prior art probes methods, where the size of clonable fragments limits "movement" along a DNA segment from a known gene region to about 40 kilobases with a single cloned probe.

Using methods described in the earlier application, it is possible to construct a cluster of such probes which are capable of binding to a series of widely spaced (20–2,000 kilobase) gene regions along a section of genomic DNA. The cluster is prepared by generating a succession of probes, each of which has a "downstream" segment which overlaps the "upstream" segment of the previously obtained probe, so that the probes are pairwise overlapping at each of the widely spaced gene regions. Ideally, it would be desirable to produce a cluster of probes which span the entire human genome, say at 200–1,000 kilobase intervals. The cluster would allow for rapid screening of polymorphisms related to genetic diseases, and would also facilitate gene mapping generally, since any genomic region would have a corresponding probe which could be used in generating a series of more closely spaced probes, by similar probe generation methods.

The present invention is concerned with improved junction hopping probes and methods for generating a cluster of probes which "span" a major section of genomic DNA, i.e., which bind to gene regions along the DNA section at widely spaced intervals, preferably between about 100–1,000 kilobases. The present invention is aimed particularly at improved methods for mapping the positions and distances between gene regions which bind the probes, and for constructing finer resolution restriction maps of any of the DNA segments which lie between two such gene regions on the genomic DNA.

In producing the improved junction or hopping probes of the present invention, the initial genomic digest is formed by digesting the genomic material to completion with a rare-site endonucleases, i.e., an endonucleases that cuts the DNA at infrequent sites, rather than by partial endonucleases digestion, as in the earlier described method. Fragments are formed by first digesting a genomic DNA material of interest where the initial genomic fragments used in constructing the probes are formed by complete digestion of DNA at an infrequent restriciton site, rather than by partial digestion at a relatively common cutting site. The restriction enzyme used to produce the genomic fragments is selected to produce an average size of genomic restriction fragments, which will, of course, determine the spacing between genomic gene regions for which a probe exists. For example, XhoI would produce average size genomic fragments of about 200 kilobases; Sfi and Hlu, fragments whose average size is about 500 kilobases; and NotI, fragments which average sizes of about 1,000 kilobases. The complete-digest fragments are then circularized and selected for relatively small hopping probes, as above, to produce a cluster of hopping probes, each of which is homologous to the end regions of one of the large rare-site genomic fragments.

The usefulness of the probe cluster in certain important applications requires that the probes be mapped or ordered as to their corresponding binding regions on the genomic DNA. With these ordered probes, any specific region of the genome can be investigated with the corresponding probe, and any probe-binding events, such the discovery of a disease-related polymorphism can be assigned to a particular region of genome according to the hopping probe involved. Some of the uses of an ordered set of hopping probes are explored in the earlier-filed parent application. Other uses, which are related to the present invention, will be described below.

According to one aspect of the present invention, the hopping probes can be ordered by a novel probe screening method which also involves a cluster of a second type of probe, referred to herein as linking probe, each of which spans the rare cutting site at which genomic DNA was cut in forming the hopping probes. That is, if the hopping probes were generated from fragments cut at the rare cutting site X, each of the linking probes is capable of binding to one of the sites X and to regions immediately upstream and downstream of this cutting site. It can be appreciated then that the linking probes can bind to the downstream region of one DNA segment defined by the X sites sites, and the upstream region of the immediately adjacent (in a downstream direction) segment defined by X sites. The hopping probes, by contrast, are homologous to the opposite end regions, of any one such segment. Novel methods for producing such linking probes are also described herein.

In the method for ordering the hopping probes, one of the hopping probes is labeled, and used to probe for the set of linking probes, by conventional hybridization blotting techniques. The hopping probe, being homologous to the end regions of one genomic restriction fragment, will bind to each of the two linking probes which are homologous to the opposite end regions of that genomic fragment. This probing establishes the two linking probes as corresponding to adjacent rare restriction sites. One of these linking probes is now labeled and used to probe the set of hopping probes, to identify the second hopping probe which is homologous to the linking probe. This second hopping probe is now used to probe the set of linking probes, and this procedure is continued in a stepwise fashion, with each new hopping probe being used to identify the next-adjacent linking gene, and each new linking probe being used to identify the next-adjacent hopping probe.

The hopping probes of the invention are also useful, according to another aspect of the invention, for constructing restriction maps of the corresponding long genomic fragments. In this method, a selected long restriction fragment is partially digested to cut the fragment into a number of complete or partial digest fragments of the restriction endonuclease being examined. These fragments are then size fractionated, yielding an electrophoretic gel pattern whose bands correspond to the shortest restriction fragment in the long genomic fragment, to the entire long fragment itself. This pattern is now probed separately with each of the upstream and downstream segments of the hopping probe, yielding with the upstream segment, a pattern of progressively larger molecular weight bands which all include the upstream restriction fragment, and with the downstream segment, a pattern of progressively larger fragments which all include the downstream restriction fragment. By using size and position data obtained from both patterns, a relatively accurate measure of restriction site positions and distanced can be obtained.

These and other objects and features of the invention will be more fully apparent when the following detailed description of the invention is read in conjunction with the accompanying drawings.

DETAILED DESCRIPTION OF THE INVENTION

Figure 1:
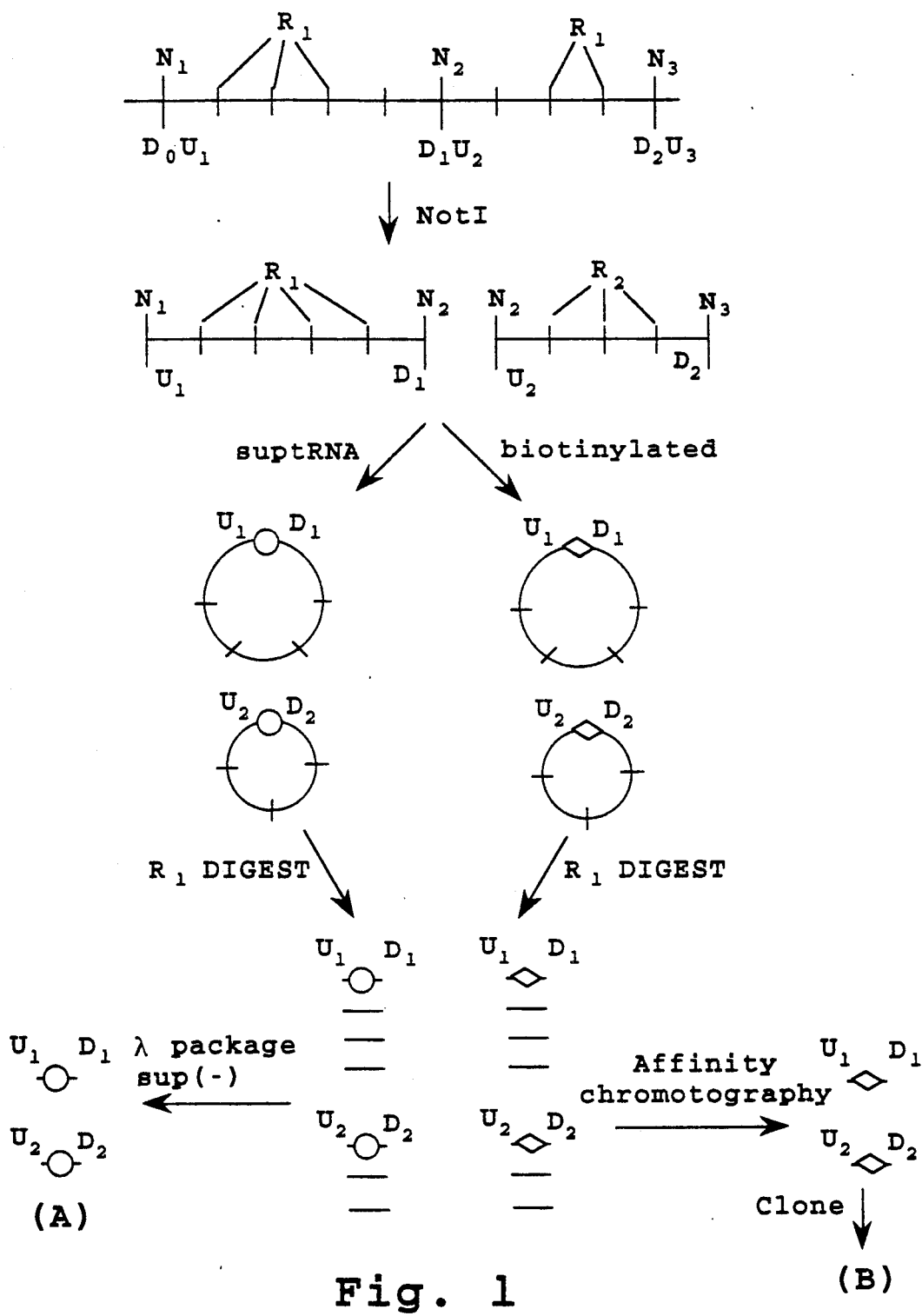
FIG. 1 illustrates preferred methods for producing hopping probes according to the invention, which include (A) inclusion of a selectable marker or (B) an affinity probe into large genomic fragments which are circularized end-to-end in forming the hopping probes.

Sections I-IV below detail steps in the construction of a cluster of probes in accordance with the invention. The steps include first, digesting strands of genomic DNA with an endonucleases (or selected pair of endonucleases) which is specific for infrequent restriction sites whose average spacing is at least about 50 kilobases, and preferably a selected spacing between about 100-2,000 kilobases, to produce genomic digest fragments whose average size is at least about 50 kilobases. Digestion methods are detailed to Section I. The large digest fragments are then ligated under conditions which lead predominantly to single-fragment circles with an end-to-end junction. The ligation reaction, including a reaction in which a intermediate segment containing either a selectable marker or ligand is incorporated in the junction region of the single-fragment circles, is described in Section II.

Following monomer formation, the circularized DNA pieces are digested with one or more selected restriction endonucleases, according to procedures described in Section III, to produce digest fragments, a portion of which contain the junction regions of the circularized monomers. These fragments may be identified by one or a combination of selection procedures described generally in Section IV below.

Section V considers novel methods for producing a cluster of probes, referred to herein as linking probes, which span the infrequent restriction sites at which the DNA segment is cut in forming the cluster of hopping probes. The two types of probes can be used, in a method described in Section VI, to order the positions of the infrequent sites in the genomic DNA, and therefore establish the "sequence" of hopping and linking probes corresponding to these restriction sites. Finally, Section VII describes a novel method which uses a hopping probe in constructing a restriction map of the corresponding large digest fragment from genomic DNA.

I. Producing Large Genomic DNA Digest Fragments

The source of genomic DNA from which the large genomic DNA digest fragments are derived will typically be a particular cell type, cell line, or tissue containing the DNA which is to be studied. For example, investigations of the major histocompatibility complex (MHC) in man have been carried out with DNA derived from peripheral blood lymphocytes or macrophages obtained from normal individuals or individuals having known disease-related genetic defects (reference 12). Clonal sublines derived from lymphocytes, which therefore have a relatively uniform genetic composition, may be preferred. The cell line may be selected for specific chromosomal aberrations, such as a chromosomal deletion in the chromosomal regions of particular interest. To illustrate, a stable human B-lymphoblastoid cell line having a deletion of the short arm of one copy of chromosome 6 has been prepared (reference 17). This deletion is known to extend to the MHC genes for DR, DC, SB, and HLA and B. Accordingly, studies on the localization and/or organization of these genes is unambiguous as to alleles, since only one copy of the genes is present in the chromosomes from the cell line.

DNA from the cell source is isolated by standard procedures, which typically include successive phenol and phenol/chloroform extractions with ethanol precipitation, as described generally in reference 18, 19. In Example I below, peripheral blood lymphocytes derived from normal individuals were employed as a source of genomic DNA, and the DNA was isolated by successive phenol and phenol/chloroform extractions.

The isolated genomic DNA is digested to completion, under standard endonuclease digest conditions, with a restriction endonucleases which is selected to cut the DNA into digest fragments having an average size of at least about 50,000 and preferably between 100 and 2,000 kilobases. The expected average fragment size for a number of restriction endonucleases is given in reference 18. Among the preferred endonuclease enzymes are XhoI, which form fragments of about 200 kilobases average size, Sfi and Mlu, which form fragments of average size about 500 kilobases, and NotI whose fragment sizes average about 1,000 kilobases. Typical digest conditions are given in Example 1, and can be determined usually from manufacturer's specifications. Digest conditions for many endonucleases are also given in reference 18, pp 98-106.

In some applications, it may be desirable to produce hopping probes derived from a selected size class of genomic fragments only, or to preselect the hopping probes on the basis of the size fragments from which the probes were derived. For example, in gene mapping studies of the type described below, it may be advantageous to group the probes in a cluster into groups corresponding to different size ranges of genomic fragments. Fractionation of large, relatively large DNA pieces (in the approximately 50-1,000 kilobase region) is preferred carried out by pulse field gel electrophoresis, according to procedures detailed in U.S. Pat. No. 4,473,452. This electrophoretic techniques relies on a pulsed cross field to orient long, linear DNA segments out of axis with the primary field gradient, to enhance resolution, particularly at DNA sizes above about 100 kilobases. Good separation of DNA molecules up to 2,000 kilobases and larger has been achieved with this method. After electrophoretic separation, bands corresponding to selected size groups can be eluted and collected, according to conventional methods.

II. Circularizing the Large Genomic Digest Fragments

According to an important aspect of the invention, the large genomic digest fragments from above are under conditions which produce predominantly single-fragment circles with end-to-end junctions, as opposed to concatemers produced by ligating between two or more fragments. The general theory of DNA fragment ligation as it relates to monomer (single-fragment circles) and concatemer formation has been discussed (reference 23). The theory, which is based on the probability of end-ligation occurrences, predicts the concentration of DNA pieces, j, at which the probability of DNA circle formation is equal to the probability of formation of linear concatemers. For large molecular weight DNA molecules:

$$j = \frac{63.5}{(kb)^{1/2}} \mu\text{grams/ml},$$

where kb is the length of the DNA in kilobases. The equation predicts, for example, that for 100 kilobase DNA pieces, j is approximately 6 µg/ml.

The concentration of DNA pieces in the ligation reaction is selected to produce a high percentage (e.g., 95%) of circularized monomers in the completed reaction. To determine this concentration, the mixture of DNA pieces to be ligated is diluted to a number of increasingly dilute mixtures. The highest concentration is preferably about that predicted by the above equation to produce approximately equal numbers of circularized monomers and linear concatemers, and the lowest concentrations are typically between about 10 to 100 times more dilute. The various-dilution DNA mixtures are incubated with a suitable ligase enzyme, such a T4 DNA ligase, at a suitable activity concentration, such as between about 1 and 2 units per µliter, under conditions which produce substantially complete ligation. Generally, the reaction time required to achieve complete ligation will increase with longer DNA pieces.

In Example II below, the ligation of a 200 kilobase SalI genomic fragments is carried out at fragment concentrations ranging between about 5.0 and 0.1 µg/ml, in a ligation mixture also containing 1.6 units per µliter of T4 DNA ligase. The reaction is carried out at 12° C. for 12 hours, and longer for relatively large genomic fragments, as detailed in Example II. The earlier filed application also details reaction conditions suitable for producing largely circularized monomers of genomic digest fragments. In particular, the concentration of fragments needed to produce a high percentage of single-fragment end-to-end ligations, $j_x$, can be calculated as follows:

$$j_x = 0.6 \frac{(50)^{1/2}}{(x)^{1/2}} \mu\text{grams/ml}$$

Thus, for example, the concentration of DNA pieces having a molecular weight of about 180 kilobases would be about 0.3 µgrams per ml.

The specific reaction described above is one in which the DNA pieces are ligated directly end-to-end to produce circular monomers. As will be discussed below in Section IV, this approach requires probe selection based on hybridization to another group of probes, such as the linking probes described in Section V. A simpler method for probe selection, also discussed in Section IV, is based on incorporation into the circularized fragments of an intermediate segment which can itself be used to distinguish regions of fragment junction from other regions of the circularized molecules, when these are digested into relatively small clonable fragments.

More particularly, the intermediate segment is one which permits (a) biological selection of clonable-size fragments containing the marker, referred to generally as a selectable marker, (b) physical separation of marker-containing fragments, for example by affinity chromatography, referred to as a ligand marker. Preferably, the intermediate segment is sufficiently small (e.g., less than about 300 base pairs) such that it cannot self-circularize. One exemplary selectable marker includes a suppressor tRNA gene which allows amber-mutated phage lambda containing the suppressor gene to grow in suppressor-free hosts (reference 24). The suppressor tRNA gene may need to be modified by attaching linker segments capable of forming sticky-end attachment to the DNA pieces during the circularization reaction. Example II below describes the preparation of a suppressor tRNA marker having SalI sticky ends. To incorporate the suppressor gene into circularized monomers, the tRNA gene is included in the ligation reaction at a severalfold molar concentration excess with respect to the DNA concentration, and the mixture of DNA pieces and marker gene segments are ligated under the conditions described above for direct-end ligation. This method is illustrated in the upper frame (A) in FIG. 1, and described in Example III. Panel A of FIG. 1 also shows the set of restriction fragments generated by digestion of the circularized monomers ($R_1$ digest products). The fragments containing open circles represent the molecules containing the suppressor tRNA. Selection of the $R_1$ digest fragments containing the suppressor tRNA genes by lambda packaging in a sup⁻ strain results in the selection of junction-fragments. These junction-fragments represent a subset (the two end restriction fragments) of the total restriction fragments making up of the original linear molecules. Methods for selecting junction-fragments containing the suppressor tRNA in a suppressor-minus host are detailed in Section IV below.

Cos sites, which are carried in cosmid vectors, are another type of selectable marker which may be incorporated into the junction region of monomers. The essential characteristics of cosmids, and their use in cloning eukaryotic DNA fragments up to 45 kilobases, are well known (see reference 18, pp 45-54). The cosmid vector selected is preferably one which has a unique restriction endonuclease site which will allow sticky-end ligation with the DNA digest pieces. The cosmid vector is linearized at this endonuclease site, and may be further treated with alkaline phosphatase (reference 25) to prevent self-ligation in the monomerization reaction. The linearized, phosphate-treated cosmid vector is added to the DNA digest pieces, preferably at a 10-25 molar excess, and the reaction components are ligated, in the presence of a suitable ligase under conditions substantially like those described above. The reaction produces circularized monomers containing one or more junction-site cosmid vector segments. There are then subjected to partial digestion and recirculization, followed by selection of junction fragments in a conventional phage lambda cloning system, as will be described in Section IV.

Self-ligation of the cosmid vector in the circularization reaction can be minimized, as indicated above, by treating the vectors with alkaline phosphatase. A more elegant approach which avoids the problem of self-ligation of the vectors employs an approximately 18 base cos site marker segment. The cos site is preferably produced as a synthetic polynucleotide which includes sticky ends capable of ligation with the sticky-end DNA digest pieces. The ligation reaction mixture includes the DNA pieces, at the suitably low concentrations indicated above, a 10–100 fold molar excess of the sticky-end cos site, and a suitable DNA ligase. The components are reacted under conditions similar to those described above, producing circularized monomers having one or more cos sites at their junction regions. For selection purposes, the fragments are spliced into a plasmid containing an origin-of-replication site requisite for cosmid replication in a bacterial host system. The cos-site fragments are selected on this host as described in Section IV.

Ligand-type marker segments include a ligand portion or moiety capable of binding specifically and with high affinity to an anti-ligand to form a ligand/anti-ligand complex. The ligand portion may be a length of single-stranded nucleic acid capable of hybridizing with a complementary "anti-ligand" strand, or may be an antigen ligand having a specific anti-ligand binding pair. Examples of such ligand/anti-ligand pairs include antigen/antibody, carbohydrate/lectin, biotin/avidin, and DNA sequence/sequence-specific binding protein pairs. The latter type of binding pair is illustrated by the lac operator/lac repressor protein. Where the ligand moiety is an antigen ligand, the marker segment preferably includes a length of typically double-stranded DNA having one or more antigen molecules coupled covalently to the nucleic acid bases. One preferred ligand includes biotin, which binds specifically and with high affinity to both avidin and to anti-biotin antibody. A method for attaching biotin covalently to the C-5 position of uridine, to form a biotinylated dUTP, is described in reference 26. An application of the method to form a biotin-containing marker segment is described in Example IV, where the biotin molecules are incorporated, as biotinylated dUTP, into filamentous bacteriophage M13 fragments. The significance of this approach is that only one strand of DNA is biotinylated, so that the other strand can serve as parent for viable progeny. The biotinylated fragments are incorporated into circularized DNA pieces substantially as has been described for selectable marker segments. The approach is illustrated at the bottom (B) in FIG. 1.

Panel B of FIG. 1 also illustrates the selection of a subset of restriction fragments of the original circularized monomers in the junction-fragment probes. This subset of fragments consists of restriction fragments representing each end restriction fragment of the linear parent molecule (e.g., $U_1$ and $D_1$, and, $U_2$ and $D_2$).

III. Producing Hopping Probes

The circularized monomeric fragments formed in accordance with Section II are treated with a selected restriction endonuclease or endonucleases to cut the large circular fragments into clonable-size digest fragments, including digest fragments which contain the junction or end-to-end ligation region of the circularized molecule. In particular, the digest treatment should cleave the large fragment at a distance of at least about 1 kilobase, and preferably several kilobases, from the end-to-end junction region of the circularized molecule, to insure that each segment in the probe on either side of the junction region can bind by homologous base pairing to the corresponding end region in the genomic fragment from which the probe was derived. Also, the endonuclease must not cleave the the circularized molecule in the region of the junction, including any intermediate segment introduced into the junction. Finally, the fragments produced by the digestion must be of a size suitable for cloning, typically less than about 20 kilobases for lambda phage cloning, and less than about 40–50 kilobases for cosmid cloning. One preferred endonuclease for forming the digest fragments is EcoRI, which yields a heterogeneous size range of fragments up to about 15 kilobases. Typical conditions for producing digest fragments are given in Example III.

The foregoing procedures are illustrated in FIG. 1 which shows at at the left, a section of genomic DNA containing a plurality of rare restriction sites $N_1$, $N_2$, to $N_n$ which are spaced from one another along the section by an average distance of about 50–2,000 kilobases, depending on the specific restriction sequence representing the N-site. Each segment $F_i$ bounded by each pair of sites $N_i$, $N_{i+1}$ has an upstream end region $U_i$ and a downstream region $D_i$ which each border the associated $N_i$ and $N_{i+1}$ sites, respectively. Also shown in each segment are a series of internal relatively frequency restriction sites, such as EcoRI sites.

As seen in the figure, initial digestion with the N-site endonuclease releases a series of $F_i$ segments, all bounded by N-sites. These are then circularized, as described in Section II, to form large circularized monomers, preferably under conditions leading to the incorporation at the end-to-end junction, of a selectable marker, such as the tRNA suppressor gene shown at the top, or a ligand marker, such as the biotinylated marker shown at the bottom of the figure. To form the junction or hopping probes of the invention, these circularized fragments are cleaved by at the relatively frequent, e.g., EcoR1, sites, to release relatively small fragments, some of which contain the end-to-end junction (and the intermediate segment introduced at the junction, and a much greater number of fragments derived from internal regions of the large genomic fragment. Method for isolating the junction fragments from internal fragments are considered below in Section IV. At this point it is only important to note the junction or hopping probe contains a first segment derived from the upstream region of the fragment $F_i$ between the $N_i$ site and the immediately downstream restriction site used in releasing the junction fragments, and a second segment derived from the downstream region of the same fragment between the $N_{i+1}$ site and the immediately upstream site at which the digest fragments were released.

More generally, given a section of DNA of the form shown in FIG. 1, containing a series of restriction sites $N_i$ which are spaced from one another by an average distance of between about 100–2,000 kilobases, and $U_i$ and $D_i$ regions immediately downstream and upstream of the corresponding $N_i$, respectively, the invention includes one or a cluster of probes $N_i$, each capable of binding by homologous base pairing independently to $U_i$ and the adjacent $D_{i+1}$ regions of the DNA section. Each probe in the cluster comprising a first segment derived from an upstream end portion of the linear fragment $N_i/N_{i+1}$ produced by digesting the DNA section to completion with an endonuclease which cuts at the infrequent restriction sites only, and a second segment derived from a downstream end portion of said linear fragment and connected adjacent its downstream end to the upstream end of the first segment. The total length of the probe is substantially less than that of the fragment from which the probe is derived and of a size that can be cloned. As the term is used herein, a probe segment is "derived from" a corresponding gene region of the linear DNA strand or section if the segment is (a) obtained directly from the corresponding gene region or (b) is produced by clonal propagation of DNA material obtained or copied from such gene region.

The first and second segments in the probe may be connected by direct ligation, or by an intermediate segment which can be used to select junction fragments released from the circularized segment.

Of course it is understood that the linear section of DNA from which the probe is actually derived is resentative of the genomic DNA of a particular species, and that the probe is intended for binding to the corresponding spaced genomic regions of DNA from any individual of that species whose DNA has the same general sequence and map positions in such regions. It will also be understood that the probe may exist in either single-strand or double-strand form, and that probe binding to the homologous region of the DNA section will take place only when both DNA section and probe are in a single-stranded form.

V. Selecting Hopping Probes

The use of single-copy probes for selecting desired junction fragments will be considered first with reference to junction fragments that have been formed by direct end-to-end ligation. As can be appreciated these probes will contain unique upstream and downstream regions of the original genomic DNA; that is, these regions will not be present in any on the internal digest fragments. Therefore, the fragment probes can be selected by probes having which are homologous to either or both of these regions, but to regions which overlap with the internal fragments. Section V below describes one such probe, referred to herein as a linking probe, which is suitable for selecting direct-ligation type junction probes. Briefly, the linking probes are constructed by cutting the genomic DNA at the relatively frequent cutting sites, e.g., at EcoRI sites, used in fragmenting the circularized genomic fragments above, yielding a small portion of fragments which span the rare cutting sites $N_i$, and a much larger number of "internal" fragments which do not. From this fragment mixture, those linking probes containing the rare cutter sites are selected, these probes then containing the upstream and downstream regions, which are also present in the junction or hopping probes.

In the selection procedure, the digest fragment from the circularized molecules are inserted into a suitable cloning vector, which is then used to transform a suitable bacterial strain host. A variety of general purpose cloning vectors, which preferably include lambda phage vectors, would be suitable. Many of these vectors are available from commercial sources, such as Vector Cloning Systems, or are widely disseminated and available on request from a variety of sources. General techniques, vector availability, and suitable bacterial host strains are discussed generally in reference 18, pp. 17-54.

Following cloning, DNA from the transformed colonies is transferred to nitrocellulose filters and hydridized, by conventional techniques with linking probes which have been radiolabeled, such as by nick translation. These procedures are outlined generally in reference 18. The cloning vectors from the selected colonies may digested to yield the probe of interest, which can be isolated and identified by the linking probe, according to standard procedures.

The isolated hopping probes may be further screened to remove probes with multiple-copy regions. This can be done by hybridizing the isolated probes, after radiolabeling, with genomic DNA which has been digested and fractioned, typically by gel electrophoresis. Multiple-copy probes will of course light up more than one band in the fractioned fragments.

FIG. 1A illustrates a procedure for selecting junction fragments which have incorporated one or more selectable marker genes, in this case the suppressor tRNA gene, into the junction region. Here the digest fragments released from the circularized vector are cloned into a lambda cloning vector containing a pair of amber mutations which can be suppressed by the tRNA gene, as evidenced by the ability of the phage to produce plaques in a suitable suppressor (−) bacterial strain. Any lac z amber bacterial strain would be suitable, including the bacterial strain CARD-15 described by Dunn, R. J., et al, J. Biol Chem. 256:6109 (1981), NK 5486 available from the Cold Spring Harbor Laboratory, Cold Spring Harbor, NY.

The host strain is plated under conditions which allow for plaque development in cells infected with suppressor (+) lambda phage, and positive colonies are picked and isolated. The method is illustrated in Example III. The suppressor-containing probe fragments can be further screened to remove multiple-copy probes as above.

A third general selection procedure, described with reference to FIG. 1B, is applicable to junction fragments containing a ligand marker segment at the junction region. Here junction fragments released from the circularized monomers by endonuclease digestion contain a ligand probe by which the junction probes can be isolated from the internal fragments. In the particular method described in Example IV, biotin-labeled junction fragments are separated from other EcoRl digest fragments by affinity chromatography on a sepharose solid support prepared to contain surface-coupled anti-biotin antibody. After fragment-binding and column washing steps, the bound fragments are released by elution with a high salt/urea solution.

The selected ligand-labeled junction fragments are spliced into a suitable cloning vector, such as bacteriophage lambda, to clone the fragment inserts. Isolated probes can be further screened to remove probes with multiple-copy segments, as above.

It can be appreciated that each of the three selection methods just described produces a cluster of gene probes which cover or substantially cover the entire genomic DNA which was used in generating the probes. That is, to the extent probes are not discarded because of multiple-copy regions, the cluster includes two probes corresponding to substantially each rare $N_i$ site in the genomic DNA—one probe which can bind by homologous base pairing to the upstream side of the site, and a second probe which can bind to the downstream side of the site.

VI. Preparation of Linking Probes

The present section is concerned with methods for preparing a cluster of linking probes, or fragments which are constructed to span a pair of hopping probes of the type described above. Such linking probes are useful in initial hopping probe selection, as discussed above, and for ordering the hipping probes, according to the sequence of $N_i$ sites on a genomic DNA section, in a method which will be detailed in section VI below.

Figure 2:
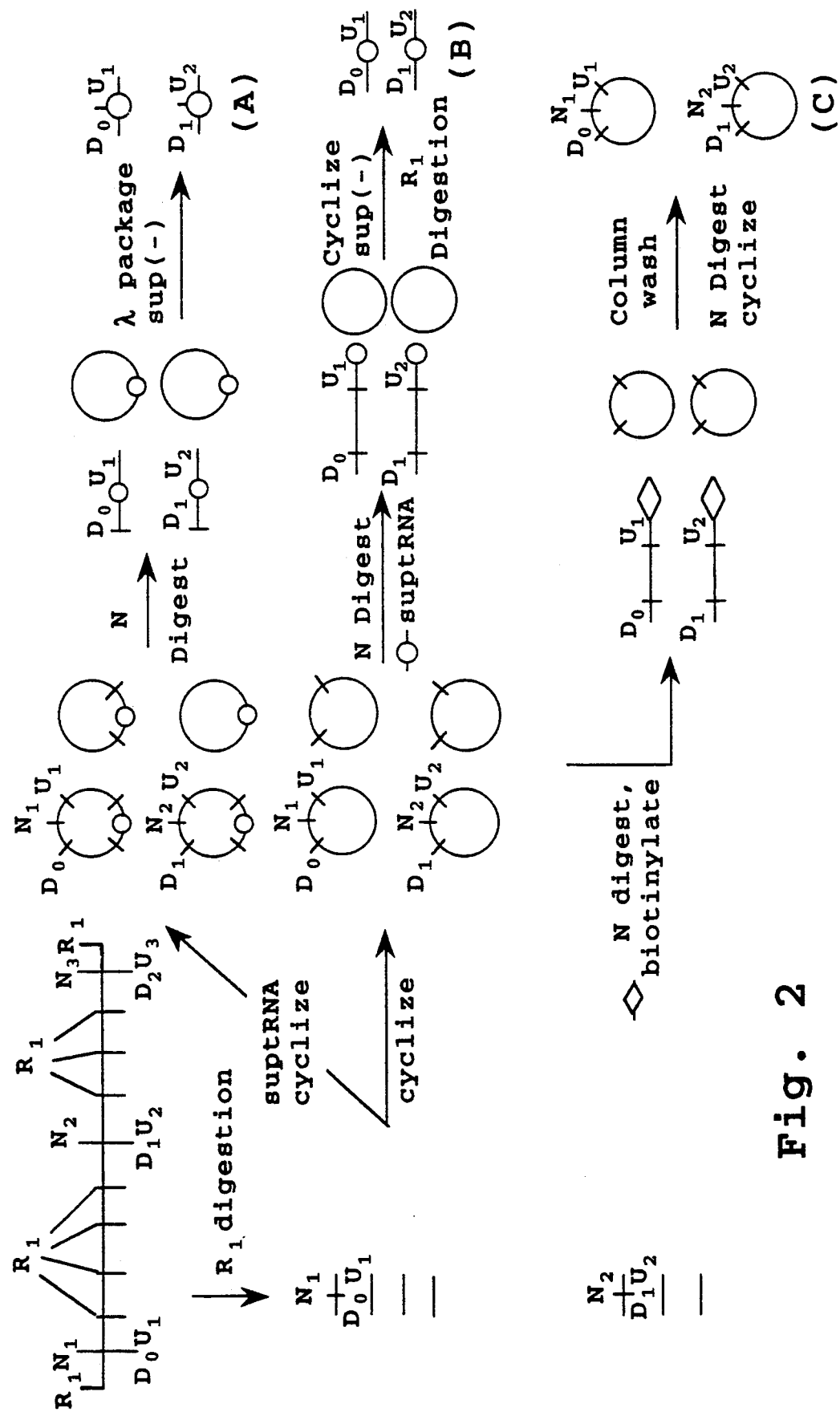
FIG. 2 illustrates preferred methods for selecting linking probes used in the invention, which include (A) introducing a selectable marker into a circularized form of a linking probe, (B) attaching an affinity probe to the rare cutting in the probe, and (C) introducing a selectable marker into the rare cutting site in the probe.

The nature of the linking probes and their overlapping relationship with the hopping probes can be understood with reference to FIG. 2, which shows a section of genomic DNA like the one shown in FIG. 1, containing a series of rare restriction sites $N_i$, which define a series of segments and fragments $F_i$ which have a selected average length between about 100-2,000 kilobases. Each segment contains a plurality of relatively frequent restriction sites, such as the tcoRI sites shown in the figure. As in FIG. 1, the frequent sites immediately adjacent each $N_i$ site define upstream and downstream regions associated with the site. Also as in FIG. 1, only relatively few of the actual number of total frequent restriction sites are shown, for purposes of simplifying the drawing. For example, if the average size of the $F_i$ fragments is 200 kilobases, and the average spacing between frequent sites is about 10 kilobases, each fragment would have an average of about 20 such sites. Therefore, the relative size of the upstream and downstream regions associated with each $N_i$ site would be much smaller than indicated, and the number of digest fragments produced by digesting the section at these sites, much larger than indicated.

Each linking probe is constructed to include an $N_i$ site and the upstream and downstream regions immediately adjacent that site. In conformity with the upstream and downstream designations used in FIG. 1, the linking probes are constructed to contain a first segment which is immediately upstream of the $N_i$ site and which is derived from the downstream end region $D_{i-1}$ of the $F_{i-1}$ segment, and a second segment which is immediately downstream of the $N_i$ site which is derived from the upstream end region $U_i$ of the $F_i$ segment. The two segments may or may not have the same relative orientation as in the genomic section, depending on the method of preparation. It can be appreciated that each linking probe spans end regions in two fragments $F_{i-1}$ and $F_i$, and therefore can bind to a pair of hopping probes each derived from one of these fragments.

In preparing the linking probes, a sample of genomic DNA, isolated by standard procedures (Example I), is digested to completion with a restriction endonuclease which cuts at the frequent restriction sites, such as the EcoRI sites, which border the rare $N_i$ restriction sites. Although EcoRI is a preferred cutter, other endonucleases which cut at at sites which are spaced less than about 10-20 kilobases or less from one another, and for which convenient cloning vectors are available, would be suitable. Such enzymes are commercially available, and their properties and recommended reaction conditions for producing complete digest fragments are usually describes by the manufacturer. Several literature references, including reference 18, at pages 97-149, are sources of additional information.

With reference to FIG. 2, the endonuclease digestion produces a number of relatively small fragments, some of which contain internal $N_i$ sites and the bordering $D_{i-1}$ and $U_i$ end regions, as indicated. These fragments will be referred to herebelow, for purposes of clarity, as EcoRI fragments, it being understood that the fragments could have been generated by another endonuclease, as above. The fragment forming step is common to each of the three probe preparation methods which will now be described.

METHOD 1

In the first method, shown at the top in the figure (FIG. 2A), the EcoRI fragments are circularized in the presence of a selectable marker, such as the tRNA suppressor marker described in Example II, under conditions which favor single-fragment end-to-end junctions. The above discussion relating to circularization of large genomic fragments is applicable. In particular, the circularization reaction is carried out at low fragment concentration, in the presence of excess selectable marker. The specific reagents and reaction conditions described in Example VI are applicable.

Following circularization, the fragments are digested to completion with the rare cutter endonuclease, to open those fragments, and only those fragments, which contain the infrequent restriction site of interest. Of course, it is necessary to use a selectable marker which is not itself cut by the rare cutter endonuclease. The mixture of circularized and cut fragments are now mixed with a suitable cloning vector under ligation conditions which allow insertion of linearized fragments only into the vector. The cloning vector is then introduced into a host in which vectors containing the inserted selectable marker can be selected. It will be appreciated that the selectable marker may include one of a number of known resistance or suppressor genes, or enzyme coding genes, which would allow selection of marker-containing vectors.

In the particular method illustrated in Example VI, the selectable marker is a tRNA suppressor gene capable of suppressing two amber mutations in a selected phage cloning vector, thereby allowing phage growth (plaque formation) in infected suppressor (−) bacterial strains. The circularized fragments are cut with the SalI, to open only those fragments containing an infrequent SalI site, and the linearized fragments are ligated into a Ch3a lambda phage at the single SalI site in the vector. The phage, following in vitro packaging, are plated on the suppressor (−) bacterial strain host W3110r−m+. After selection, the phage can be digested to release the desired linking probes, which can be isolated by electrophoretic separation. A seen at the right in the figure, the probes include the two segments $D_I$ and $U_{i+1}$ connected through the selectable marker. It can be appreciated that the two segments have a relative upstream-to-downstream orientation which is opposite to that in the genomic section, i.e., the two segments are connected at their downstream ends, in relation to their orientation in the genomic section. This orientation is also different from that of the hopping probes, where the downstream end of the "downstream" segment is connected to the upstream end of the "upstream" segment.

METHOD 2

In the second method, which is illustrated in FIG. 2B, the genomic digest fragments from above are cloned into a vector which is also designed for clonal selection based on inclusion of a selectable marker in the inserted fragment. Here however, the fragment is first introduced into a cloning vector and allowed to propagate on a bacterial host under conditions in which the presence of the selectable marker is not required. If necessary, the plasmid is also modified, for example by selected site mutagenesis, to eliminate any restriction sites which would be cut by the rare cutter endonuclease of interest. In Example V, the cloning vector is the P3 plasmid derived from W3110r−m+, which contains a kanamycin resistance gene and two amber-mutated antibiotic resistance genes. The vector is modified, according to conventional techniques, to remove unneeded sequences, and if necessary, any SalI sites. The genomic digest fragments are cloned into the P3 plasmid which is then used to transform a suppressor (−) host, but in the absence of the antibiotics against which resistance is conferred by the amber mutations.

After cloning, the vectors are cut with the rare cutter endonuclease, e.g. SalI as in Example V, to open the vector at the unique site within the genomic fragment. Vectors with "internal" genomic fragments remain circularized. These vectors, including a small proportion of linearized vectors, are now diluted and incubated in the presence of excess selectable marker under ligation conditions which favor single-fragment circularization. The reaction conditions discussed in Section II above are applicable. The selectable marker is chosen, as above, to allow selection in a suitable host. The selectable marker used in Example V is the above tRNA suppressor having EcoRI linker ends. The mixture of circularized plasmids, some of which now contain a selectable marker introduced at the rare cutting site, are now grown on a host under conditions which allow selection for plasmids which have incorporated the marker. In Example V, this selection is based on the appearance of colonies capable of growing on kanamycin and the two antibiotics which are related to the plasmid amber mutations. Plasmids from the selected colonies are isolated and may be digested as above, to allow for isolation of the desired probe fragments.

The steps in the second method are illustrated in FIG. 2B. As seen, the method yields linking probes having $D_{i-1}$ and $U_i$ segments which are connected through a selectable marker, The probes differ from those produced by the first method in that the upstream-to-downstream orientation of the two segments is the same as that in the genomic DNA section.

METHOD 3

The third method for producing linking probes is a variant of the second method, in which a ligand (binding) intermediate segment is substituted for a selectable marker, for use in fragment selection. The method, which is illustrated in FIG. 2C, follows that of method 2 through the cloning of the digest fragments in a suitable cloning plasmid. Here, however, the plasmid need not be adapted for selection based on incorporation of a selectable marker, since the purpose of the plasmid is only to generate clonal genomic DNA fragments. Therefore, the clonal vector may be any general purpose plasmid whose construction, availability, and use is described, for example, in reference 18. The only requirement for the plasmid is that it (a) can accommodate fragments of the size introduced, typically less than about 15 kilobases, and (b) that it does not itself contain rare restriction sites of the site selected for in the linking fragments.

After ligating the fragments in the above plasmids, the plasmids are digested with the selected rare-cutter endonuclease, linearizing only those plasmids containing a potential linking probe fragment. The linearized fragments are now ligated with a ligand segment, such as a biotinylated DNA segment, under conditions which lead to ligand attachment to the cut plasmid ends. The ligand segment end sequences are preferably such that the rare site is regenerated by attachment of the segment to each end of the cut plasmid. This allows the plasmid to be released readily from an affinity binding column by digestion with the rare-site cutter, and also serves to regenerate the original linearized plasmid after plasmid isolation.

Selection of desired probes is now carried out by conventional affinity chromatography or the like, to yield fragments which contain an internal rare-cutter sites. The general considerations and methods described above and in Example IV for the construction of biotinylated segments, and isolating of biotin containing fragments are applicable. However, as just noted, the ligand-bound species is preferably released from the anti-ligand support by endonuclease digestion. The resulting isolated fragments now include the original linearized cloning construction, and this can be recircularized, as above, and propagated in a compatible bacterial host. The linking probes each have the same general structure as those produced by method 2 herein, except that the $D_{i-1}$ segment is connected directly to the $U_i$ segment, but where the upstream and downstream segments have the same orientation as in the genomic section from which the probe was derived.

VI. Ordering Hopping or Linking Probes

Figure 3:
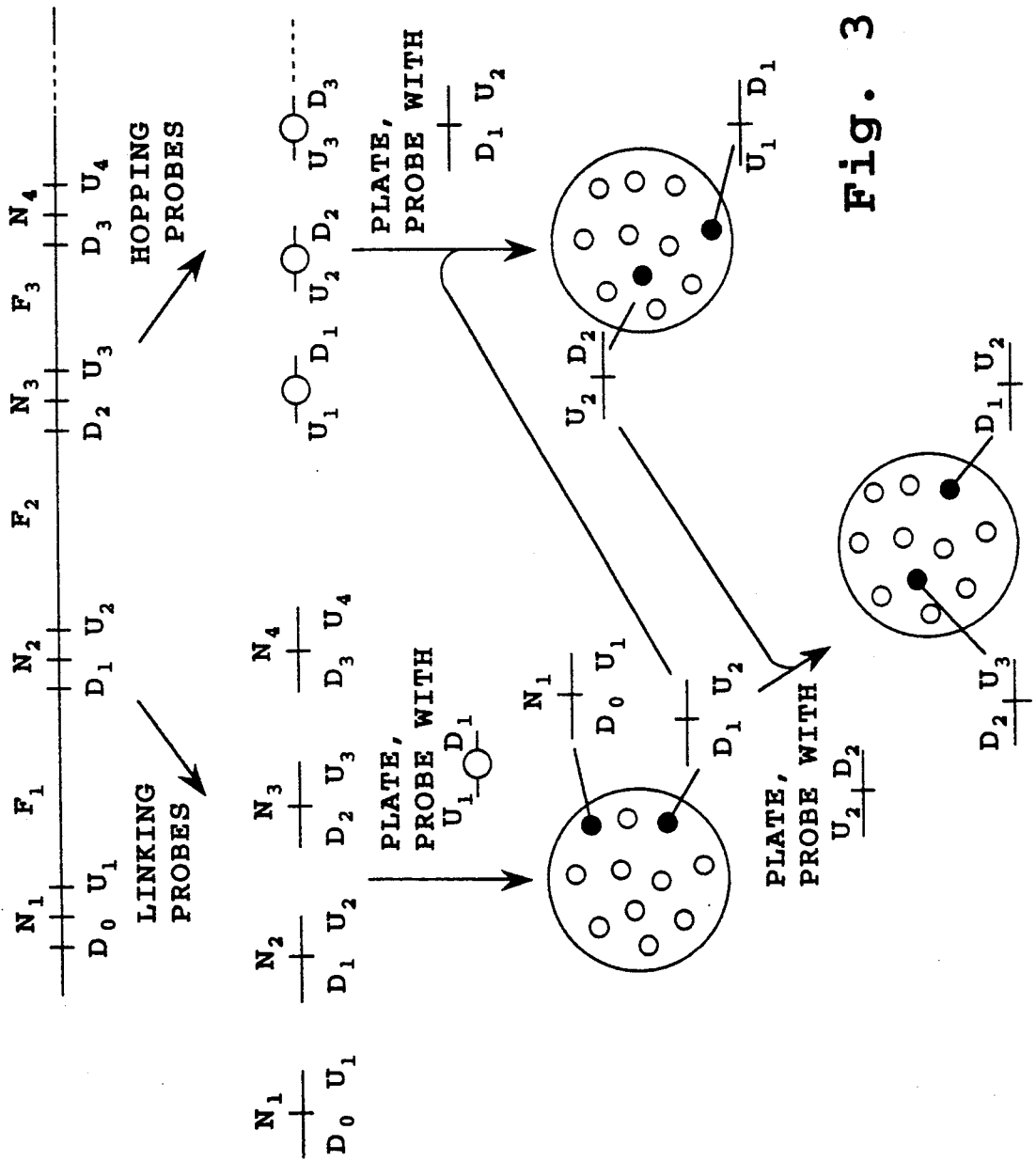
FIG. 3 illustrates how a cluster of linking probes and a cluster of hopping probes are used to order the sequential map positions of the probes in each cluster.

FIG. 3 illustrates a method which utilizes a cluster of linking probes, prepared as in Example V, to order a cluster of hopping probes, prepared as in Example VI. Here the term "ordering" is used to indicate that the individual probes are assigned a sequence corresponding to the sequence of $N_i$ sites on the genomic DNA to which the probes bind. As will be seen, the method results in the ordering of both types of probes.

In paracticing the method, the probes of one cluster, e.g., the linking probes, are plated in cloned form, as shown at A in FIG. 3, giving colonies corresponding to each probe. The DNA from the separate colonies is then transferred onto a nitrocellulose filter, according to standard techniques, and hybridized with a selected one of the hopping probes, which have been radiolabelled, e.g., by nick-translation. This technique, which is generally referred to as Southern blotting, is carried out conventionally. In the figure, the selected hopping probe is designated $U_i/D_i$. It is understood that this designation is arbitrary, and that the hopping probe may in fact be chosen randomly from any position along the sequence of $N_i$ sites.

The $u_i/D_i$ hopping probe will hybridize with the two linking probes which span each of the $N_i$, $N_{i+1}$ sites defining the $F_i$ fragment from which the hopping probe was derived. One of these linking probes $D_0/D_1$ is downstream of $F_i$ and the other $D_1/U_2$ is upstream of the fragment. One of the two linking probes is arbitrarily chosen, which then establishes the direction of "hopping" which the method proceeds along. Assuming that the upstream $D_1/U_2$ linking probe is selected, the probes will be ordered upstream of the $F_i$ site. It will be understood that downstream ordering would also be performed independently by "hopping" with $D_0/U_1$ downstream linking probe.

The selected $D_i/U_2$ linking probe is radiolabelled, and now used to probe the set of hopping vectors, which are plated and transferred to nitrocellulose filters, as above. Since the linking probe spans across one of the $N_i$ sites, it will hybridize with two of the hopping probes—the probe $U_1/D_1$ just downstream of the $N_1$ site, and the $U_2/D_2$ probe just upstream of this site. The method has now identified two hopping probes which bind to adjacent $F_i$ fragments on the genomic DNA. Both of these probes can be compared, by restriction analysis, to the first $U_1/D_1$ hopping probe used, to identify that probe as a reference. The second $U_2/D_2$ probe is then used to reblot the linking probes, to identify the two linking probes $U_1/D_2$ and $U_2/D_3$ which are spanned by the new hopping probe. A comparison of the identified probes or blott positions indicates which of the two probes is the next-adjacent $U_2/D_3$ probe. The linking probe screening is alternated with the hopping probe screening in this manner until a desired number of probes have been ordered, or until the system breaks down, either because of multiple copy problems or because one of the probes in the series is missing.

It can be appreciated that the method provides a very simple procedures for mapping long stretches of DNA whose distances are in the megabase size range, and for establishing a set of probes which bind to selected regions within the sections.

VII. Restriction Mapping in Large Genomic Fragments

Another important application of the hopping probes described herein is for constructing restriction maps of the large genomic digest fragments used in constructing the hopping probes. This method is useful in mapping a genomic region at a finer level of detail than at the map spacings of 100 kilobases or more which are typically achieved in the method of Section VI. In a typical example, one of hopping or jumping probes will correlate with a genetic feature of interest, such as a disease-related polymorphism, which one wishes to examine at a finer level of genetic resolution.

As a first step in the method, the genomic DNA is digested to completion with the rare-site endonuclease used in forming the hopping and linking probes. The digest fragments are then fractionated, preferably by the pulse gel electrophoresis method mentioned above, to separate the large fragment into size groups which may range from 50-2,000 kilobases. The fragment if interest is identified by standard blotting techniques, using the radiolabelled probe previously identified with the gene feature of interest. The fragment so identified is eluted and may be repurified by a second electrophoretic separation, if desired.

Figure 4:
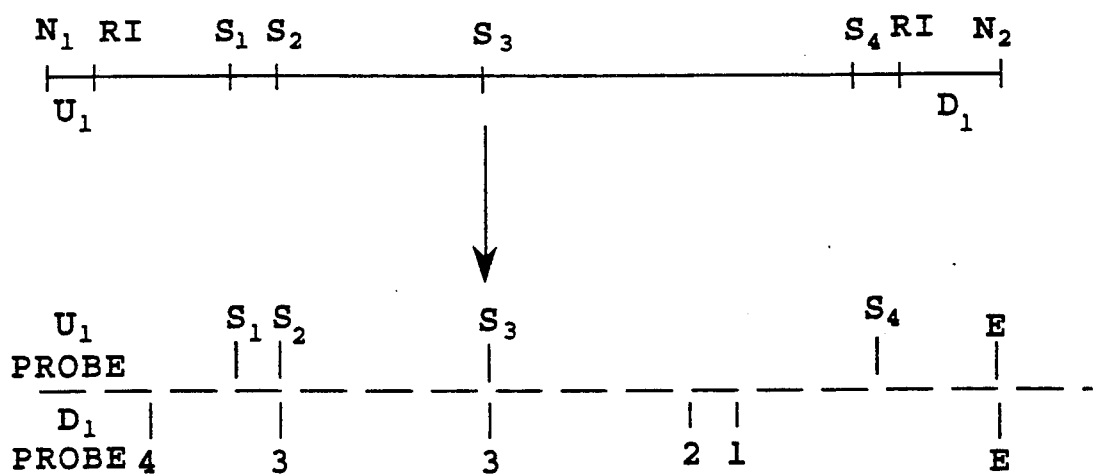
FIG. 4 illustrates how a hopping probe of the invention is used in constructing a restriction map of a large genomic fragment from which the hopping probe was constructed.

FIG. 4 show a large genomic fragment defined by rare sites $N_i$, and which has been isolated as above. The fragment contains, in addition to the relatively numerous EcoRI sites which define the boundaries of the hopping and jumping probes, a small number of sites of intermediate frequency sites $S_i$ which are to be mapped. As a first step, the purified fragment is partially digested with the endonuclease which can cut the fragment only at the $S_i$ sites. The partial digestion yields digest fragments which include the upstream end segment $N_1/S_1$ alone and with increasing numbers of internal $S_i$ sites up to the full-length $N_1/N_2$ fragment. It can be appreciated that all of the fragments in this group will bind to the upstream $U_1$ moiety of a $U_1/D_1$ hopping probe.

Another group of partial fragments produced by the digestion includes the $S_4/N_2$ fragment and increasingly larger fragments containing additional upstream $S_i$ sites, up to the full length $N_2/N_1$ fragment. All of the fragments in this group will bind the the upstream $D_1$ moiety of the same hopping probe.

To map the $S_i$ sites according to the invention, the partial fragments are first size fractionated, preferably by pulse gel electrophoresis, as above. The fractionated bands are now transferred to a filter and blotted with each $U_i$ and $D_1$ moiety of the probe. The probes are prepared by cleaving the hopping probe at a known site in its region of junction, and radiolabelling the two probe halves, as above.

When the fractionated partial digest fragments are probes with the upstream probe, the group of fragments containing the upstream $N_1/S_1$ give the pattern shown above the dotted line in the figure, where the $S_i$ designation indicates the position of an $N_1/S_i$ fragment. From this pattern, the sizes of the various fragments can be calculated, and from this, the map distance between adjacent $S_i$ sites. The filter can now be freed of the first probe and hybridized to the second downstream probe $D_1$, yielding the pattern shown below the dotted line in the figure. Here $S_i$ indicates the position of an $N_2/S_i$ fragment. This pattern similarly allows the map distances between adjacent $S_i$ sites to be determined.

An advantage of the present method is that relatively accurate map distances are established at both end of the fragment, since estimation is done at both ends at relatively low molecular weight regions of the gel pattern. Another advantage is that the two sets of distance relationships provide an internal check that all of the $S_i$ sites are represented.

The following examples illustrates various method for preparing the hopping and linking probes of the invention. The examples are intended to illustrate, but in no way limit the scope of the invention.

BACTERIAL STRAINS AND VECTORS

The following bacterial strains can be obtained from the American Type Culture Collections (ATCC), 12301 Parklawn Drive, Rockville, Md. 20852: strain LE392, (ATCC #33572); strain W3110r−m+(P3) (ATCC #39084); and strain MC1061 (ATCC #39083); Bacterial strain CARD-15 and pRD69 can be prepared as described in Dunn, R. J., et al, J. Biol. Chem. 256:6109–6118 (1981). Lambda phage Ch16A and Ch3a are available on request from Dr. Fred Blattner, University of Wisconsin Laboratory of Genetics, 445 Henry Mall, Madison, Wis. 53706.

EXAMPLE I

Preparation of Genomic DNA Fragments

This example describes the preparation of genomic DNA SalI restriction digest fragments. Peripheral blood lymphocytes are derived from normal individuals and the genomic DNA is isolated by successive phenol and phenol/chloroform (1:1) extractions, as described generally in reference 19. The DNA is suspended in a standard digest buffer to a concentration of about 0.1 mg/ml, and digested to completion with SalI. The digest buffer includes 150 mM NaCl, 6 mM Tris-HCl, 6 mM MgCl$_2$, and 6 mM mercaptoethanol, pH 7.9, and digestion is carried out for 60 minutes at 37° C. The SalI is inactivated by heat treatment at 70° C. for 15 min. The digested DNA is extracted with phenol/chloroform, and precipitated with 70% ethanol. The size distribution of the fragments is analyzed by pulse field gel electrophoresis, according to published procedures (Carle, G. F., et al., Science 232:65 (1986)).

EXAMPLE II

Preparation of Suppressor tRNA Marker Segment

This example describes the preparation of a suppressor tRNA marker segment having SalI ends. The segment is adapted for incorporation into the end-to-end junctions in circularized monomers of DNA genomic fragments, as illustrated in Example III below.

Plasmid pRD69 (Dunn, supra) containing the gene for an amber suppressor tRNA is a pBR322 plasmid containing a synthetic tRNA which has been widely applied in the πVX cloning system (reference 32). The suppressor tRNA gene is the pRD69 construct terminates at EcoRI sites, and is obtained as an EcoRI fragment purified by electrophoresis on agarose gel. The purified suppressor gene, which is 207 base pairs in length, is blunt-ended by treatment with E. coli DNA polymerase, Klenow fragment, in the presence of all four deoxynucleotide triphosphates. Phosphorylated SalI linkers having the sequence pGGTCGACC are obtained from New England Biolabs (Beverly, Mass.). The linkers are ligated to the blunt ends of the suppressor gene substantially according to the procedure described in reference 43. The addition of the SalI linkers, which begin with a guanosine base, destroys the EcoRI sites in the suppressor gene. The nucleotide sequence of the suppressor and attached SalI linkers is confirmed by ligating a copy of the suppressor gene into the SalI site of bacteriophage M13mp8 and determining the nucleotide sequence of the resulting phage by dideoxy sequencing (reference 44).

The suppressor gene is ligated into the SalI site of pBR322 and the suppressor-containing plasmid is transfected into bacterial strain CARD-15 which contains an amber mutated lac gene. Plating the transfected bacteria on MacConkey's agar, (Difco) containing lactose demonstrates that the suppressor gene retained its function. Approximately 1 mg of the plasmid is prepared, and the suppressor gene insert is obtained by SalI digestion, followed by electrophoretic separation on 1.4% agarose, and electroelution.

EXAMPLE III

Incorporation of Suppressor tRNA into Circularized Fragments

This example describes the circularization of the SalI fragments (Example I), in the presence of the suppressor tRNA gene fragment from Example II, to form circularized monomers containing one or more suppressor tRNA gene fragments at the end-to-end circle junction sites. Bacterial host E. coli strain MC1061 or W3110 r-m+, which contains no suppressor genes of its own, and a second bacterial host, E. coli strain LE392, a suppressor positive strain, are obtained as above.

A reaction mixture including the SalI fragments, at five selected concentrations of 0.01, 0.03, 0.1, 0.3, and 1 μ/ml the suppressor tRNA at a molar concentration about 500 times that of the DNA insert, and T4 DNA ligase, at a concentration of about 1.6 units per μl is prepared in a standard ligase buffer. The mixture is incubated at 12° C. for 12–48 hr. following ligation, the DNA is ethanol precipitated, resuspended in a standard digestion buffer, and digested to completion with EcoRI, releasing EcoRI junction fragments containing the two SalI/EcoRI end segments from the circular molecules. The EcoRI fragments are ligated into lambda Ch16A under standard conditions, followed by in vitro packaging, and plating on either bacterial host MC1061 (the suppressor-strain) or LE392. DNA from plaques which grow on MC1061 are then analyzed by restriction analysis for the presence of the SalI suppressor fragment. These phage contain the desired hopping probes in cloned form.

EXAMPLE IV

Incorporation of Biotinoylated Polynucleotide in Circularized Genomic Fragments This example describes a method for incorporating a biotin-labeled polynucleotide marker segment into the junction region of circularized monomers of DNA pieces. A biotin-labeled polynucleotide segment is prepared as described in reference 26. Briefly, there is synthesized an analog if dTTP containing the biotin molecule covalently linked to the C-5 position of the pyrimidine ring through an allyl-amine link. A biotinolated gene segment is formed from a short length of the filamentous bacteriophage M13, which has been copied in the presence of biotin-labeled dTTP, to form a biotinlabeled, double-stranded genome. Experimentally, M13 bacteriophage is copied by incubation with all four deoxynucleotides plus biotin-labeled dTTP which is present at a molar ratio of about 1:4 with respect to each of the other deoxynucleotides, in the presence of T4 DNA polymerase. After heat-inactivating the polymerase, the double-stranded bacteriophage is treated with a selected restriction endonuclease, such as HaeIII, which contains only C and G bases in its recognition sequence, and which therefore can act normally on double-stranded DNA containing biotin-labeled thymidine. The double-stranded material is digested to completion with the selected restriction endonuclease, under standard conditions, and small molecular weight pieces (preferably less than about 300 base pairs) are isolated by gel electrophoresis using 1.4% agarose gel. The fragments obtained are digested to completion with EcoRI and made blunt-ended by reaction with E. coli polymerase, Klenow fragment, in the presence of all four doexynucleotides as described in Example V. The SalI linkers of Example II are attached to the fragment ends under conditions like those described in Example III. Fragments having sizes less than about 100 bases are removed electrophoretically. The resulting fragments contain biotin-labeled, double-stranded DNA having SalI sites at their opposite ends.

The biotin-labeled fragments are incorporated into the junction-region of the SalI genomic fragments from Example I under conditions substantially like those described in Example III. A reaction mixture containing about 0.2 μg/ml of the DNA insert pieces and an approximately 500-fold molar excess of the biotin-labeled pieces are incubated in the presence of 14 ligase at about 12° C. for 12–48 hr., after which the circularized DNA pieces are isolated by ethanol precipitation. The precipitated circularized monomers are resuspended in a suitable digest buffer and digested to completion with EcoRI, also as described in above Example III, to hopping probes with an internal SalI site.

The biotin-labeled hopping probes are separated from the other EcoRI digest fragments by affinity chromatography using antibody-sepharose, prepared by coupling anti-biotin antibody to cyanogen bromide-activated sepharose 4B, as described in reference 45. Columns containing the resin are equilibrated with a suitable buffer, such as 10 mM Tris HCl, pH 7.5 and the DNA samples are applied to the column in the same buffer, then washed with several volumes of the same buffer. These conditions are effective to bind substantially all of the biotin-labeled EcoRI fragments to the column. The bound biotin-labeled fragments are eluted from the column with 6M urea/1M NaCl. Alternatively biotin-labeled fragments could be bound by anti-biotin antibody and purified over a column of *Staphylococcus aureas* protein A as described in references 26 and 29.

EXAMPLE V

Production of SalI Linking Probes

Method 1

This example describes the generation of a cluster of genomic probes containing internal SalI restriction sites.

DNA is isolated and digested to completion with EcoRI according to the general procedures in Example I. The EcoRI fragments are cloned into the EcoRI site of a plasmid derived from the P3 plasmid from W3110 r-m+ (P3) by directed deletion of unwanted sequences and elimination of any SalI sites. The modified plasmid has a kanamycin resistance gene, and amber-mutated ampicillin and tetracycline resistance genes. The library of plasmids is then digested with SalI. A molar excess of SalI ended suppressor tRNA (Example II) is added, followed by dilution and addition of T4 ligase, as in Example IV. The ligation mixture is used to transform *E. coli* W3110 r-m+ (suppressor−). Selection of colonies capable of growth on all three antibiotics resulted in the isolation of plasmids containing the suppressor tRNA and adjacent SalI sites. SalI containing EcoRI fragments, which are the desired linker fragments, can be isolated by digestion with EcoRI of suppressor containing plasmids.

EXAMPLE VI

Production of SalI Linking Probes

Method 2

A suppressor tRNA gene terminating at EcoRI sites is prepared substantially as in Example II, mixed with the EcoRI genomic fragments from Example V, and ligated under conditions like those in Example III to form circular molecules containing single digest fragments circularized with a tRNA suppressor junction. Following ligation, the DNA is ethanol precipitated and resuspended in a standard digest buffer.

The circularized fragments are treated with SalI, under standard conditions, to open those fragments which contain an internal SalI site in the genomic fragment. The SalI treated fragments are then ligated into λCH3A, which has a single SalI site, under standard conditions, followed by in vitro packaging and plating on a suppressor (−) bacterial hose, as in Example V.

Any phage which grows contains a suppressor tRNA and a linking probe. The presence of the tRNA gene can be confirmed by suppression of a lac z amber gene, as described (reference 18). The positive plaques are selected, and the linking probes isolated by EcoRI digestion and electrophoretic separation, according to standard procedures.

While preferred embodiments of the invention and its method of use have been described it will be apparent to those skilled in the art that a variety of changes and modifications can be made without departing from the invention.

It is claimed:

1. A probe comprising:
    a first DNA segment (1) derived from the upstream end region of a linear DNA fragment obtained by digestion of genomic DNA to completion with a restriction endonuclease which cuts at sites that occur infrequently, said DNA fragment having upstream and downstream end regions which are spaced from one another by between about 100 kilobases to 2,000 kilobases, and (2) which is effective to bind by homologous base pairing to said upstream end region in genomic DNA; and,
    a second DNA segment (1) derived from the downstream end region of said DNA fragment and connected adjacent its downstream end, as defined by the upstream-to-downstream orientation in the DNA fragment, to the upstream end of the first segment, and (2) which is effective to bind by homologous base pairing to said downstream end region in genomic DNA;
    where the probe represents a subset of restriction fragments of said DNA, and the probe is of a size which can be cloned.

2. The probe of claim 1, wherein the first and second segments are joined through an intermediate segment which is not derived from said DNA fragment.

3. The probe of claim 1, wherein the intermediate segment is a selectable marker segment which allows probe selection in a cloning system.

4. The probe of claim 3, wherein the selectable marker segment is a suppressor tRNA which allows for selection of a phage vector containing the probe in suppressor minus host.

5. The probe of claim 2, wherein the intermediate segment is a ligand adapted to bind specifically and with high affinity to an anti-ligand.

6. The probe of claim 5, wherein the ligand is biotin, and the anti-ligand is avidin or anti-biotin antibody.

7. The probe of claim 1, wherein the restriction endonuclease is selected from the group consisting of NotI, SfiI, SalI, and MluI.

8. The probe of claim 1, wherein the upstream and downstream gene regions in the DNA fragment are each single-copy regions.

9. The probe of claim 1, wherein said first and second segments are connected by direct ligation to one another.

10. A method of forming a probe capable of binding by homologous base pairing independently to an upstream gene region, which is present on a linear section of genomic DNA and which binds by homologous base pairing to a selected probe, and to a downstream gene region, which is also present on said section and is spaced from the upstream gene region by a distance of about 100–2,000 kilobases, said method comprising:
    digesting the genomic DNA to completion with a restriction endonuclease which cuts at sites that occur infrequently to produce genomic fragments, where at least some of said fragments have said upstream and downstream regions at their opposite ends,
    ligating the genomic fragments under fragment concentration conditions which favor circularization of single fragments into circular DNA species with connected fragment ends,
    digesting the circular DNA species by restriction endonuclease treatment to release digest fragments which are of a size which can be cloned, and which include fragments containing such connected fragment ends intact, cloning the digest fragments, and isolating cloned digest fragments which contain the connected fragment ends, and which are able to bind by homologous base pairing to the selected probe.

11. The method of claim 10, wherein said ligating is carried out in the presence of a selectable marker, which is adapted to join the cut ends of the genomic fragments, to produce circularized fragments each having one or more such selectable marker connecting the fragment ends to each other.

12. A method of ordering restriction fragments along a DNA segment comprising: providing a pool of hopping probes representative of the DNA segment, each hopping probe containing a first DNA segment (1) derived from the upstream end region of a linear DNA fragment obtained by digestion of the DNA segment to completion with a restriction endonuclease which cuts at sites that occur infrequently, said DNA fragment having upstream and downstream end regions which are spaced from one another by between about 100 kilobases to 2,000 kilobases, and (2) which is effective to bind by homologous base pairing to said upstream end region in genomic DNA; and, a second DNA segment (1) derived from the downstream end region of said DNA fragment and connected adjacent its downstream end, as defined by the upstream-to-downstream orientation in the DNA fragment, to the upstream end of the first segment, and (2) which is effective to bind by homologous base pairing to said downstream end region in genomic DNA;

where the probe represents a subset of restriction fragments of said DNA, and the probe is of a size which can be cloned;

providing a pool of linking probes representative of the DNA segment, obtained by digesting the DNA segment with a restriction endonuclease whose cut site does not overlap with the cut site of the restriction enzyme used to generate the hopping probes; and, alternately hybridizing a selected linking probe to the pool of hopping probes to identify a pair of hopping probes which have regions of homologous overlap with the selected linking probe, and then hybridizing one of the identified hopping probes with the pool of linking probes, to identify a pair of linking probes which have homologous regions of overlap with the one hopping probe, at each hybridization step, identifying the next-in-sequence hopping or linking probe, and using the next-in-sequence probe in the next hybridization step.

13. The hopping probe of claim 12, wherein the restriction endonuclease which cuts at sites that occur infrequently is selected from the group consisting of NotI, SfiI, SalI, and MluI.

14. The method of claim 12, wherein providing the pool of linking probes includes the steps of digesting the DNA segment with a restriction endonuclease which cleaves the segment into fragments of about 20 kilobases or less, and isolating those fragments which contain an internal cut site of the restriction enzyme used to generate the hopping probes.

15. The method of claim 14, wherein said isolating includes cloning the fragments in a circular cloning vector, linearizing the vectors with an endonuclease which cuts at the internal cut site of the restriction enzyme used to one or both ends of the linearized vector, and isolating those vectors containing the binding sequence.

16. The method of claim 15, wherein the binding sequence is biotinylated, and said isolating is based on specific binding of the linearized, biotin-containing vectors to a solid support having attached avidin or antibiotin antibody.

17. The method of claim 14, wherein said isolating includes cloning the fragments in a circular cloning vector, linearizing the vector with a restriction endonuclease which cuts specifically at the internal cut site of the restriction enzyme used to generate the hopping probes, introducing a selectable marker into the linearized vectors, and selecting vectors containing the selectable marker.

18. The method of claim 17, wherein the selectable marker is a suppressor tRNA and the vectors are selected on the basis of growth in a suppressor minus bacterial host.

19. The method of claim 14, wherein said isolating includes circularizing the digest fragments in the presence of a selectable marker, digesting the circularized fragments with a restriction endonuclease which cuts specifically at the internal cut site of the restriction enzyme used to generate the hopping probes, introducing the cut vectors into a cloning vector, and selecting cloning vectors which contain the selectable marker.

20. A family of sequence-overlapping probes derived from a segment of genomic DNA comprising:

a first DNA segment (1) derived from the upstream end region of a linear DNA fragment obtained by digestion of the DNA segment to completion with a restriction endonuclease which cuts at sites that occur infrequently, said DNA fragment having upstream and downstream end regions which are spaced from one another by between about 100 kilobases to 2,000 kilobases, and (2) which is effective to bind by homologous base pairing to said upstream end region in genomic DNA; and.

a second DNA segment (1) derived from the downstream end region of said DNA fragment and connected adjacent its downstream end, as defined by the upstream-to-downstream orientation in the DNA fragment, to the upstream end of the first segment, and (2) which is effective to bind by homologous base pairing to said downstream end region in genomic DNA, where the probe represents a subset of restriction fragments of said DNA, and the probe is of a size which can be cloned; and, a pool of linking probes representative of the DNA segment, obtained by digesting the DNA segment with a restriction endonuclease whose cut site does not overlap with the cut site of the restriction enzyme used to generate the hopping probes.

* * * * *